(12) United States Patent
Matsumura et al.

(10) Patent No.: US 8,496,714 B2
(45) Date of Patent: Jul. 30, 2013

(54) BASE MATERIAL FOR REVASCULARIZATION

(75) Inventors: Goki Matsumura, Tokyo (JP); Yoshito Ikada, Kyoto (JP); Yuki Sakamoto, Kyoto (JP); Shojiro Matsuda, Kyoto (JP)

(73) Assignee: Gunze Limited, Kyoto (JP)

( * ) Notice: Subject to any disclaimer, the term of this patent is extended or adjusted under 35 U.S.C. 154(b) by 165 days.

(21) Appl. No.: 13/056,239

(22) PCT Filed: Jul. 28, 2009

(86) PCT No.: PCT/JP2009/063438
§ 371 (c)(1),
(2), (4) Date: Mar. 25, 2011

(87) PCT Pub. No.: WO2010/013717
PCT Pub. Date: Feb. 4, 2010

(65) Prior Publication Data
US 2011/0172757 A1    Jul. 14, 2011

(30) Foreign Application Priority Data
Jul. 29, 2008  (JP) ................................ 2008-195409

(51) Int. Cl.
*A61F 2/82* (2006.01)
(52) U.S. Cl.
USPC ........................................ 623/23.75; 424/423
(58) Field of Classification Search
USPC ........... 623/1.42–1.48, 23.72–23.75; 424/423
See application file for complete search history.

(56) References Cited

U.S. PATENT DOCUMENTS

| | | | |
|---|---|---|---|
| 8,137,686 B2 * | 3/2012 | Kladakis et al. | 424/423 |
| 2005/0002915 A1 * | 1/2005 | Atala et al. | 424/93.21 |
| 2007/0190108 A1 * | 8/2007 | Datta et al. | 424/423 |
| 2008/0176206 A1 | 7/2008 | Shinoka et al. | |
| 2010/0055781 A1 | 3/2010 | Shinoka et al. | |
| 2011/0091515 A1 * | 4/2011 | Zilberman et al. | 424/409 |

FOREIGN PATENT DOCUMENTS

| | | |
|---|---|---|
| JP | 2001-78750 | 3/2001 |
| JP | 2005-34239 | 2/2005 |
| JP | 2005-185529 | 7/2005 |
| JP | 2005-229906 | 9/2005 |
| WO | WO2008/088042 | 7/2008 |

OTHER PUBLICATIONS

Lim S.H., et al., Tissue-Engineered Blood Vessels With Endothelial Nitric Oxide Synthase Activity, Journal of Biomedical Materials Research, Part B, Applied Biomaterials, May 2008, vol. 85, Vo. 2, pp. 537-546.
Cho S.W., et al., Preliminary experience with tissue engineering of a venous vascular patch by using bone marrow-derived cells and a hybrid biodegradable polymer scaffold, Journal of Vascular Surgery, 2006, vol. 44, No. 6, pp. 1329-1340.

* cited by examiner

*Primary Examiner* — Suzette J Gherbi
(74) *Attorney, Agent, or Firm* — Hamre, Schumann, Mueller & Larson, P.C.

(57) ABSTRACT

The present invention aims to provide a material for revascularization which enables the regeneration of a blood vessel at an extremely high efficiency by being transplanted into a defect of the blood vessel.
The present invention provides a tubular material for revascularization comprising a foamed body comprising a bioabsorbable material, a reinforcing member comprising a bioabsorbable material for reinforcing the foamed body, and a reinforcing yarn comprising a bioabsorbable material for reinforcing the foamed body, wherein the reinforcing yarn and the reinforcing member are located at the center or outer face of the foamed body, the inner face thereof is the foamed body, the reinforcing yarn is wound around in a spiral-shaped, ring-shaped or X-shaped manner, and the reinforcing yarn comprises a glycolide-ε-caprolactone copolymer.

7 Claims, 2 Drawing Sheets

BASE MATERIAL FOR REVASCULARIZATION

TECHNICAL FIELD

The present invention relates to a material for revascularization which enables the regeneration of a blood vessel at an extremely high efficiency by being transplanted into a defect of the blood vessel.

BACKGROUND ART

Presently, those clinically used as artificial blood vessels are non-absorbable polymers such as Gore-Tex. Such artificial blood vessels can exhibit extremely similar physical properties to those of blood vessels and have achieved a certain result in short-term revascularization. However, an artificial blood vessel using a non-absorbable polymer has a problem that a foreign matter semi-permanently remains in the body and it results in easy formation of a blood clot and therefore it is necessary to continuously administer an anticoagulant or the like. Further, particularly in the case of use for a child, there are problems that it is needed to undergo surgery again due to size mismatch as the child grows and that re-surgery is required because of calcification of the artificial blood vessel.

To deal with the problems, recently, methods for regeneration of tissues by so-called regenerative medical techniques have been tried. That is, trials for regenerating patient own tissues by utilizing the cell proliferation mechanism of the patient itself in the scaffold of an artificial blood vessel are performed by transplantation of the artificial blood vessel which is easy to be penetrated with cells into a defect of a blood vessel.

In order to apply such a regenerative medical technique to a revascularization technique, the present inventors have developed a material for revascularization containing a foamed body including a bioabsorbable polymer and a reinforcing material including a bioabsorbable polymer as a core material incorporated in the foamed body (Patent Document 1). With respect to this material for revascularization, the foamed body becomes a scaffold where cells are firmly bonded and the reinforcing material plays a role of keeping strength enough to stand the blood flow during the time until a blood vessel is regenerated after the transplantation and also plays a role as a reinforcing material standing sutura. Since both of the foamed body and the reinforcing material include bioabsorbable polymers, the materials are absorbed after revascularization and thus it is made no need to continuously use an anticoagulant or the like in the late term. Furthermore, it is also expected that the regenerated blood vessel can be grown since the regenerated blood vessel is of own tissues. Actually, the material for revascularization has been regarded to be extremely significant in terms of clinical use. However, for actual clinical application, needless to say, a further improved revascularization efficiency and reliability have to be aimed.

PRIOR ART DOCUMENT

Patent Document

Patent Document 1: Japanese Kokai Publication 2001-78750 (JP-A 2001-78750)

SUMMARY OF THE INVENTION

Problems to be Solved by the Invention

In the case where an artificial blood vessel is transplanted, whether blood vessel tissues can be regenerated or not depends on easiness of cell penetration into the artificial blood vessel and no coarctation occurrence until the blood vessel tissues are regenerated. In order to make the penetration with cells easy, it is required for a material of the artificial blood vessel to be flexible and have a high water-absorbing property. On the other hand, in the tissue regeneration process, since coarctation is caused by tensile force of the proliferated cells toward the lumen, a tubular artificial blood vessel is required to have mechanical strength sufficient for preventing squeeze, that is, the tubular body is required to exhibit high compressive elasticity modulus when compressed and to keep the diameter. In such a manner, the flexibility and high water-absorbing property and the high compressive elasticity modulus are in a trade-off relation and difficult to realize compatibility. Further, in the case where the compressive elasticity modulus of the artificial blood vessel is high for a long time, there is another problem, "calcification", that the regenerated blood vessel becomes hard.

The present invention aims to provide a material for revascularization which is easy to be penetrated with cells, hard to be squeezed, and at the same time prevented from calcification and enables the regeneration of a blood vessel at an extremely high efficiency by being transplanted into a defect of the blood vessel.

Means for Solving the Problems

The present invention is a tubular material for revascularization comprising a foamed body comprising a bioabsorbable material, a reinforcing member comprising a bioabsorbable material for reinforcing the foamed body, and a reinforcing yarn comprising a bioabsorbable material for reinforcing the foamed body; wherein the reinforcing yarn and reinforcing member are located at the center or outer face of the foamed body, the inner face thereof is the foamed body, the reinforcing yarn is wound around in a spiral-shaped, ring-shaped or X-shaped manner, and the reinforcing yarn comprises a glycolide-ε-caprolactone copolymer.

Hereinafter, the present invention will be described in more detail.

The material for revascularization of the present invention includes a foamed body including a bioabsorbable material (hereinafter, simply referred to as "foamed body"), a reinforcing member including a bioabsorbable material for reinforcing the foamed body (hereinafter, simply referred to as "reinforcing member"), and a reinforcing yarn including a bioabsorbable material for reinforcing the foamed body (hereinafter, simply referred to as "reinforcing yarn").

The above-mentioned foamed body plays a role as a scaffold where cells penetrate and are bonded and proliferated and tissues are regenerated.

The pore diameter of the foamed body is required to be such an extent that cells easily penetrate the pores and proliferate and at the same time blood leakage is scarcely caused in the case of transplantation into a defect of a blood vessel and concretely, the lower limit is preferably 5 μm and the upper limit is preferably 100 μm. If the pore diameter of the foamed body is less than 5 μm, the cells are sometimes impossible to penetrate the pores of the foamed body and if it exceeds 100 μm, blood leakage is sometimes caused in the case of transplantation. The lower limit of the pore diameter of the foamed body is more preferably 10 μm and the upper limit is more preferably 50 μm.

The average pore diameter of the above-mentioned foamed body is measured by a conventional method, for example, a mercury penetration method, an image analysis method, or the like.

The thickness of the foamed body is not particularly limited; however the lower limit is preferably 0.3 mm and the upper limit is preferably 1.5 mm. If the thickness of the foamed body is less than 0.3 mm, the compressive elasticity modulus is low and coarctation tends to be caused easily in some cases when the tubular body is compressed and if it exceeds 1.5 mm, the flexibility is deficient and the water absorption coefficient is lowered and cell penetration becomes difficult in some cases. The lower limit of the thickness of the foamed body is more preferably 0.4 mm and the upper limit is more preferably 1.2 mm.

Examples of the bioabsorbable material constituting the above-mentioned foamed body include polyglycolides, polylactides (D, L, or DL form), polycaprolactones, glycolide-lactide (D, L, or DL form) copolymers, glycolide-ε-caprolactone copolymers, lactide (D, L, or DL form)-ε-caprolactone copolymers, as well as polydioxanones, glycolide-lactide (D, L, or DL form)-ε-caprolactone copolymers, and the like. Particularly, lactide (D, L, or DL form)-ε-caprolactone copolymers are preferable. These bioabsorbable materials may be used alone or two or more of them may be used in combination.

The above-mentioned foamed body may be subjected to a hydrophilic treatment. The hydrophilic treatment makes the cell penetration easier.

The above-mentioned hydrophilic treatment is not particularly limited and examples thereof include plasma treatment, glow discharge treatment, corona discharge treatment, ozone treatment, surface graft treatment, ultraviolet radiation treatment, and the like. Particularly, plasma treatment is preferable since the treatment remarkably improves the water absorption coefficient without changing the appearance of the material for revascularization.

The above-mentioned reinforcing member plays a role of keeping strength enough to stand the blood flow and intravascular pressure (blood pressure) during the time until a blood vessel is regenerated after transplantation by reinforcing the foamed body as well as a role of improving suture retention ability at the time of suturing with the blood vessel.

The reinforcing member is not particularly limited if it has higher strength than that of the foamed body and examples thereof include a fibrous body, a nonwoven fabric-like body, a film-like body, and the like. Particularly, a fibrous body such as a weft knitted fabric, a warp knitted fabric, a braid or a woven fabric produced by knit and weave fibers including a bioabsorbable material is preferable.

Examples of the bioabsorbable material constituting the above-mentioned reinforcing member include polyglycolides, polylactides (D, L, or DL form), polycaprolactones, glycolide-lactide (D, L, or DL form) copolymers, glycolide-ε-caprolactone copolymers, lactide (D, L, or DL form)-ε-caprolactone copolymers, as well as polydioxanones, glycolide-lactide (D, L, or DL form)-ε-caprolactone copolymers, and the like. These bioabsorbable materials may be used alone or two or more of them may be used in combination. Further, the bioabsorbable material constituting the reinforcing member may be the same as or different from the bioabsorbable material constituting the foamed body.

The thickness of the fibers constituting the reinforcing member is not particularly limited; however, the lower limit is preferably 15 denier and the upper limit is preferably 500 denier. If the thickness of the fibers constituting the reinforcing member is less than 15 denier, suturing sometimes becomes impossible at the time of suturing with a blood vessel of a living body and if it exceeds 500 denier, the above-mentioned reinforcing member cannot be produced in some cases. The lower limit of the thickness of the fibers constituting the reinforcing member is more preferably 20 denier and the upper limit is more preferably 450 denier.

The above-mentioned reinforcing yarn plays a role of reinforcing the foamed body and keeping strength enough to stand compression from the blood flow, lungs, and other organs in the surroundings and tensile force toward the lumen during the time until a blood vessel is regenerated after transplantation.

The reinforcing yarn may be a monofilament yarn and a multi-filament yarn and since having higher bending elasticity and excellent durability to compression force, the monofilament yarn is preferable.

The thickness of the reinforcing yarn is not particularly limited; however, the lower limit is preferably 0.2 mm and the upper limit is preferably 0.7 mm. If the thickness of the reinforcing yarn is less than 0.2 mm, the compressive elasticity modulus is low and coarctation tends to be caused easily in some cases when the tubular body is compressed and if it exceeds 0.7 mm, the flexibility is deficient and it sometimes results in difficulty for use as the material for revascularization. The lower limit of the thickness of the reinforcing yarn is more preferably 0.25 mm and the upper limit is more preferably 0.5 mm.

The bioabsorbable material constituting the reinforcing yarn is a glycolide-ε-caprolactone copolymer. The glycolide-ε-caprolactone copolymer is a relatively "hard" resin with an elasticity modulus of about 630 MPa and, on the other hand, has a half-life period of strength of 1 to 2 weeks and accordingly has a property that it is decomposed within a relatively short time to sharply decrease the strength. Use of the reinforcing yarn including the glycolide-ε-caprolactone copolymer provides sufficient strength for a while from the transplantation and prevents squeezing of the material for revascularization and coarctation of the blood vessel and on the other hand, the reinforcing yarn is decomposed and absorbed to lose the strength when a blood vessel is regenerated to a certain extent and further deposition of minerals can be prevented since the material does not remain and accordingly, "calcification" is efficiently prevented.

Further, owing to low compatibility of the glycolide-ε-caprolactone copolymer with the above-mentioned foamed body and its decomposition within a relatively short time, the glycolide-ε-caprolactone copolymer is supposed to be separated from the foamed body within a short time after transplantation. Use of the reinforcing yarn including the glycolide-ε-caprolactone copolymer provides sufficient strength for a while from the transplantation and prevents squeezing of the material for revascularization and coarctation of the blood vessel and on the other hand, the reinforcing yarn is separated from the foamed body when a blood vessel is regenerated to a certain extent. The foamed body from which the reinforcing yarn is separated can be expanded and contracted in accordance with proliferation of cells, so that the regeneration of a blood vessel is not inhibited. It is also supposed to result in efficient prevention of "calcification".

In addition, although the cause is not made clear, if the reinforcing yarn is subjected to coating or the like for improving the compatibility with the foamed body, it rather results in coarctation or the like in some cases. Accordingly, the above-mentioned reinforcing yarn is preferably one consisting of merely the glycolide-ε-caprolactone copolymer without being subjected to coating or the like.

The composition ratio of the glycolide-ε-caprolactone copolymer constituting the reinforcing yarn is preferably a ratio (mole ratio) of glycolide:ε-caprolactone of 90:10 to 45:55. If the ratio of glycolide exceeds 90, the reinforcing yarn becomes hard and brittle and is decomposed too fast and it is not preferable for regeneration of blood vessel tissues. On the other hand, if the ratio of ε-caprolactone exceeds 55, the reinforcing yarn becomes too much flexible, so that the reinforcing effect is small and further, the decomposing rate is retarded, so that it results in occurrence of "calcification".

With respect to a positioning relation between the foamed body and the reinforcing member, the reinforcing member is located at the center or outer face of the tubular body, which is the material for revascularization of the present invention, and the inner face of the tubular body is the above-mentioned foamed body. According to such a configuration, the reinforcing member can sufficiently play a roll of keeping strength and promote regeneration of a blood vessel from the inner side thereof to carry out early revascularization.

The above-mentioned reinforcing yarn is wound around such a composite of the foamed body and the reinforcing member in a spiral-shaped, ring-shaped or X-shaped manner. Arrangement of the reinforcing yarn in the above-mentioned state provides the material for revascularization to be obtained with further difficulty in squeezing. The reinforcing yarn may be located in the center of the foamed body or in the outer most face.

In the case where the reinforcing yarn is wound in a spiral-shaped or ring-shaped manner, the lower limit of the winding pitch is preferably 1 mm and the upper limit is preferably 10 mm. If the winding pitch of the reinforcing yarn is less than 1 mm, it sometimes becomes a cause of "calcification" or a cause of retardation of revascularization and if it exceeds 10 mm, it sometimes results in difficulty of attaining a sufficient reinforcing effect. The lower limit of the winding pitch of the reinforcing yarn is more preferably 2 mm and the upper limit is more preferably 8 mm.

The inner diameter and length of the tubular body, which is the material for revascularization of the present invention, may be selected in accordance with the aimed blood vessel.

The lower limit of the thickness of the material for revascularization of the present invention is preferably 0.3 mm and the upper limit is preferably 1.5 mm. If the thickness of the material for revascularization is less than 0.3 mm, it sometimes result in difficulty of attaining sufficient strength to stand the blood flow or sutura sometimes becomes difficult and if it exceeds 1.5 mm, the time taken for absorption is vainly prolonged and it sometimes becomes a cause of calcification.

A method for producing the material for revascularization of the present invention is not particularly limited; however examples thereof include a method of installing the previously prepared reinforcing member in a mold, pouring and freezing a solution of a bioabsorbable material forming the foamed body in the mold, and thereafter freeze-drying the material (a freeze dry method); a method of attaching a mixed solution of a water-soluble substance and a bioabsorbable material forming the above-mentioned foamed body to the previously produced reinforcing member and then drying the solution, and thereafter washing out the water-soluble substance by water washing (an elution method); and the like. In the freeze dry method, foamed bodies having various pore diameters can be produced in accordance with the freezing temperature, the polymer concentration, or the like. In the elution method, the pore diameter of a foamed body can be controlled by adjusting the particles of a water-soluble substance.

Since the material for revascularization of the present invention is obtained by reinforcing a foamed body including a bioabsorbable material with a reinforcing member including a bioabsorbable material against the outward force and further reinforcing the foamed body with a reinforcing yarn including a bioabsorbable material against the inward force, the foamed body can be a scaffold where cells penetrate and are bonded and the reinforcing member and the reinforcing yarn play a role of keeping strength enough to stand the blood flow during the time until a blood vessel is regenerated after transplantation. On the other hand, since the bioabsorbable material constituting the reinforcing yarn is a glycolide-ε-caprolactone copolymer, decomposition occurs quickly and it does not cause "calcification".

The material for revascularization of the present invention can regenerate a blood vessel at an extremely high efficiency by being transplanted into a defect of the blood vessel.

At the time of transplantation, the material for revascularization of the present invention may be transplanted as it is. Even if the material for revascularization of the present invention is transplanted as it is without inoculation of cells, the foamed body of the material for revascularization of the present invention becomes a good scaffold and is penetrated easily with cells to regenerate a blood vessel.

Further, in the case where transplantation is carried out after previous inoculation of cells such as vascular endothelial cells, bone marrow cells, vascular smooth muscle cells and fibroblast cells, earlier revascularization can be expected.

Effects of the Invention

The present invention provides a material for revascularization which enables the regeneration of a blood vessel at an extremely high efficiency by being transplanted into a defect of the blood vessel.

MODE FOR CARRYING OUT THE INVENTION

Figure 1:
FIG. 1 is an image of a tissue section of the transplanted part of the material for revascularization obtained in Comparative Example 1 stained by Nishiyama method.

Hereinafter, aspects of the present invention will be described in more detail with reference to examples; however it is not intended that the present invention be limited to the examples.

Example 1

A plain-knitted fabric formed cylindrically by using a polyglycolide yarn with 140 denier was attached to a rod made of a fluororesin with an outer diameter of 10 mm. The rod to which the plain-knitted fabric was attached was immersed in a 4% by weight dioxane solution of an L-lactide-ε-caprolactone copolymer (mole ratio 50:50) and frozen at −80° C. and thereafter subjected to freeze dry at −40° C. to 40° C. for 12 hours to obtain a foamed body. Next, while being reversed, the foamed body was separated from the rod made of a fluororesin and again attached to the rod made of a fluororesin. A monofilament yarn (thickness 1-0) of a glycolide-ε-caprolactone copolymer (ratio of glycolide:ε-caprolactone (mole ratio) 75:25) as a reinforcing yarn was wound in a spiral-shaped manner at 3 mm pitch around the surface of the foamed body. The foamed body around which the monofilament yarn was wound was immersed in a 4% by weight dioxane solution of an L-lactide-ε-caprolactone copolymer (mole ratio 50:50) for 30 seconds and frozen at −80° C. and thereafter subjected to freeze dry at −40° C. to 40° C. for 12 hours. A material for revascularization with a sandwich structure having a foamed layer with a thickness of 0.9 mm was obtained by the above-mentioned method.

Comparative Example 1

A material for revascularization was obtained in the same manner as in Example 1, except that a monofilament yarn (thickness 0.4 mm and USP size 1-0) of an L-lactide-ε-caprolactone copolymer was used as a reinforcing yarn.

Reference Example 1

A material for revascularization was obtained in the same manner as in Example 1, except that a monofilament yarn (thickness 0.4 mm and USP size 1-0) of a glycolide-ε-caprolactone copolymer coated with an L-lactide-ε-caprolactone copolymer (mole ratio 50:50) was used as a reinforcing yarn.

In this connection, the coating was carried out by immersing the monofilament yarn of a glycolide-ε-caprolactone copolymer in the 4% by weight dioxane solution of an L-lactide-ε-caprolactone copolymer (mole ratio 50:50) and thereafter drying the monofilament yarn.

(In Vitro Evaluation)

The strength needed to compress each of the obtained tubular materials for revascularization until the diameter became ½ was measured. If the value is higher, it means that the material for revascularization has higher diameter retention force to coarctation.

Further, force of 200 g was repeatedly applied in the direction in which the diameter was compressed and the number of times until each of the materials for revascularization was transversely squeezed and could not keep the shape was measured.

The results are shown in Table 1.

TABLE 1

|  | Reinforcing yarn | Winding method | Compressive elasticity modulus test | |
|---|---|---|---|---|
|  |  |  | Force needed for ½ compression (g) | Number of times until shape could not be retained |
| Example 1 | Glycolic acid-ε-caprolactone copolymer | Spiral-shaped manner | 218 | 107 |
| Comparative Example 1 | L-lactide-ε-caprolactone copolymer | Spiral-shaped manner | 320 | 153 |
| Reference Example 1 | Glycolic acid-ε-caprolactone copolymer (with coating) | Spiral-shaped manner | 270 | 139 |

(Evaluation by Animal Experiment)

The materials for revascularization obtained in Example, Comparative Example, and Reference Example were evaluated by an animal experiment with the following method.

A portion of inferior vena cava of each beagle dog with a weight around 10 kg was resected and transplanted with each of the materials for revascularization obtained in Example, Comparative Example, and Reference Example. Eleven specimens were used for Example 1: four specimens for Comparative Example 1: and eight specimens for Reference Example 1 to carry out the experiment and the number of surviving specimens after 6 months from the transplantation was measured.

The configuration of the blood vessel was recorded by angiographic examination after 6 months from the transplantation and thereafter specimens were sacrificed and the occurrence of ascites was observed with eye observation. Further, the respective transplanted parts (regenerated blood vessel parts) were touched with fingers to evaluate the presence or absence of sclerosis lesions and also the presence or absence of calcification by macro observation. Furthermore, tissue sections were produced and histologically evaluated with a microscope and also the presence or absence of calcification was evaluated by Nishiyama method or von Kossa method.

The results are shown in Table 2.

TABLE 2

| | | | Results of animal experiment | | | |
|---|---|---|---|---|---|---|
| | Reinforcing yarn | Winding method | Number of surviving specimens after 6 months from transplantation | Presence or absence of coarctation | Presence or absence of ascites | Calcification |
| Example 1 | Glycolic acid-$\epsilon$-caprolactone copolymer | Spiral-shaped manner | 11/11 | None | None | None |
| Comparative Example 1 | L-lactide-$\epsilon$-caprolactone copolymer | Spiral-shaped manner | 4/4 | None | None | Occurred in all of 4 specimens |
| Reference Example 1 | Glycolic acid-$\epsilon$-caprolactone copolymer (with coating) | Spiral-shaped manner | 4/8 | None | None | None |

Figure 2:
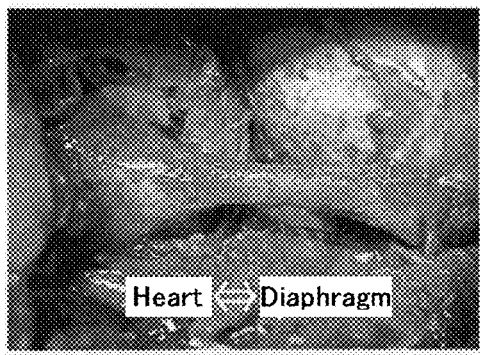
FIG. 2 is an incision image of the transplanted part after the material for revascularization obtained in Example 1 was transplanted and each sample was sacrificed after 13 months from the transplantation.
Figure 2:
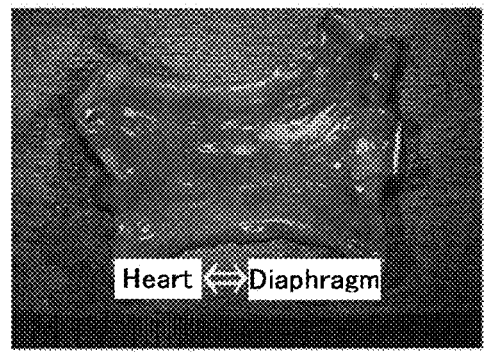
Figure 3:
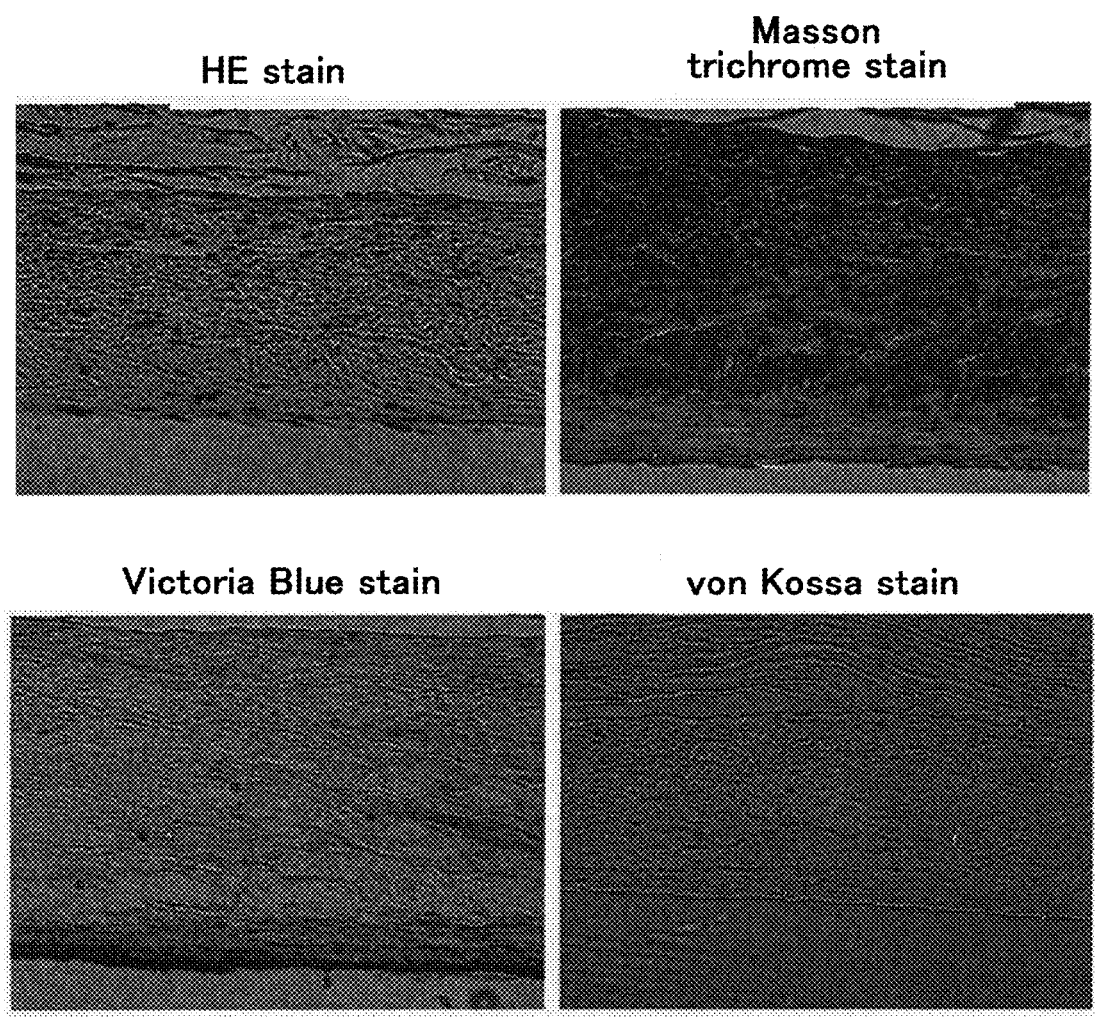
FIG. 3 is an image of the stained transplanted part after the material for revascularization obtained in Example 1 was transplanted and each sample was sacrificed after 13 months from the transplantation.

According to Table 2, in the case where the materials for revascularization of Example 1 and Comparative Example 1 were transplanted, the survival rate after 6 months from the transplantation was 100% and neither coarctation nor ascites was observed. However, in the case of using the material for revascularization of Example 1, no calcification was observed, whereas apparent calcification was observed for all of the specimens in the case of using the material for revascularization of Comparative Example 1. A tissue section of the transplanted part of the material for revascularization obtained in Comparative Example 1 was produced and an image of the tissue section stained by Nishiyama method was shown in FIG. 1. In Example 1, a good opening property of the blood vessel and production of tissues histologically extremely similar to those of a venous vessel were confirmed and no calcification was observed. In Comparative Example 1, calcification was observed and although a function as a duct was obtained; however there was a histological problem. FIG. 2 shows an incision image of the transplanted part after the material for revascularization obtained in Example 1 was transplanted and each sample was sacrificed after 13 months from the transplantation. FIG. 3 shows an image of the stained transplanted part.

In the case of transplantation of the material for revascularization of Reference Example 1, the survival rate after 6 months from the transplantation was 50% and specimens (4 dogs) survived for 6 months or longer after the transplantation were investigated to find neither coarctation nor ascites. However, in the case where the specimens died within 6 month from the transplantation were investigated, coarctation and ascites were observed in all of four dogs.

Experimental Example

Materials for revascularization were obtained in the same manner as in Example 1, except that the thickness of the monofilament yarn of a glycolide-$\epsilon$-caprolactone copolymer to be used as the reinforcing yarn was changed to 1-0 (0.4 to 0.5 mm), 2-0 (0.35 to 0.4 mm), and 3-0 (0.25 to 0.3 mm) and the compressive elasticity modulus was evaluated.

The results are shown in Table 3.

TABLE 3

| Thickness of reinforcing yarn | Compressive elasticity modulus test (Force needed for ½ compression (g)) |
|---|---|
| 1-0 | 218 |
| 2-0 | 160 |
| 3-0 | 84 |

INDUSTRIAL APPLICABILITY

According to the present invention, a material for revascularization which enables the regeneration of a blood vessel at an extremely high efficiently by being transplanted into a defect of the blood vessel can be obtained.

The invention claimed is:

1. A tubular material for revascularization comprising
   a foamed body comprising a bioabsorbable material;
   a reinforcing member comprising a bioabsorbable material for reinforcing said foamed body; and
   a reinforcing yarn comprising a bioabsorbable material for reinforcing said foamed body, wherein
   said reinforcing yarn and said reinforcing member are each located at a center of the foamed body or an outer face of the foamed body, wherein an inner face of the tubular material is said foamed body,
   said reinforcing yarn is wound around the foamed body in a spiral-shaped manner, a ring-shaped manner, or a X-shaped manner, and
   said reinforcing yarn comprises a glycolide-$\epsilon$-caprolactone copolymer.

2. The material for revascularization according to claim 1, wherein the foamed body comprises a lactide-$\epsilon$-caprolactone copolymer, wherein the lactide is in a D-form, a L-form, or a DL-form.

3. The material for revascularization according to claim 1, wherein the reinforcing yarn is wound in a spiral-shaped manner.

4. The material for revascularization according to claim 1, wherein the reinforcing yarn and the reinforcing member are located at the center of the foamed body.

5. The material for revascularization according to claim 1, wherein the foamed body has a pore diameter in a range of 5-100 μm.

6. The material for revascularization according to claim 1, wherein a thickness of the tubular material is in a range of 0.3-1.5 mm.

7. The material for revascularization according to claim 1, wherein the reinforcing yarn separates from the foamed body and decomposes in a biological environment during a process of the revascularization when the foamed body remains in the tubular material in the biological environment.

\* \* \* \* \*